(12) United States Patent
Lee et al.

(10) Patent No.: US 10,435,752 B2
(45) Date of Patent: Oct. 8, 2019

(54) USE OF ADCY3 FOR DIAGNOSIS AND TREATMENT OF GASTRIC CANCER

(75) Inventors: Yeon Su Lee, Gyeonggi-do (KR); Sung Ho Goh, Gyeonggi do (KR); In Hoo Kim, Gyeonggi-do (KR); Seung Hyun Hong, Gyeonggi-do (KR)

(73) Assignee: NATIONAL CANCER CENTER (KR)

( * ) Notice: Subject to any disclaimer, the term of this patent is extended or adjusted under 35 U.S.C. 154(b) by 523 days.

(21) Appl. No.: 14/411,970

(22) PCT Filed: Aug. 20, 2012

(86) PCT No.: PCT/KR2012/006606
§ 371 (c)(1),
(2), (4) Date: Dec. 30, 2014

(87) PCT Pub. No.: WO2014/014157
PCT Pub. Date: Jan. 23, 2014

(65) Prior Publication Data
US 2015/0240313 A1    Aug. 27, 2015

(30) Foreign Application Priority Data

Jul. 18, 2012 (KR) ........................ 10-2012-0078443

(51) Int. Cl.
*C12Q 1/6886* (2018.01)
*C12Q 1/527* (2006.01)
*G01N 33/574* (2006.01)
*C12N 15/113* (2010.01)

(52) U.S. Cl.
CPC ........ *C12Q 1/6886* (2013.01); *C12N 15/1137* (2013.01); *C12Q 1/527* (2013.01);
(Continued)

(58) Field of Classification Search
CPC ............ C12Q 1/6886; C12Q 2600/154; C12Q 2600/158
See application file for complete search history.

(56) References Cited

U.S. PATENT DOCUMENTS

2013/0130354 A1* 5/2013 Gidekel ............... C12Q 1/6886
435/219

FOREIGN PATENT DOCUMENTS

WO    2004005483 A2    1/2004
WO    2005100998 A2    10/2005
(Continued)

OTHER PUBLICATIONS

Ushijima, T. Nature Reviews: Cancer 5:223 (Mar. 2005).*
(Continued)

*Primary Examiner* — Diana B Johannsen
(74) *Attorney, Agent, or Firm* — Levenfeld Pearlstein, LLC

(57) ABSTRACT

The present invention relates to: a composition for detecting a gastric cancer marker comprising a preparation for measuring the expression level or methylation level of mRNA of ADCY3 or a protein thereof; a kit for diagnosing gastric cancer, containing the composition; a method for diagnosing gastric cancer by treating a biological sample with the preparation to ascertain whether a material for complementarily binding to the preparation exists and comparing the amount thereof with a control group; a composition for treating and preventing gastric cancer, containing a preparation capable of inhibiting ADCY3 polynucleotide or ADCY3 polypeptide; and a method for treating gastric cancer by administering the composition to an individual. According to the present invention, it is possible to diagnose gastric cancer with high diagnostic sensitivity and specificity using ADCY3 as a marker for diagnosing gastric cancer, and thus can greatly contribute to reducing mortality due to gastric cancer.

1 Claim, 10 Drawing Sheets
Specification includes a Sequence Listing.

(52) U.S. Cl.
CPC .............. *C12Y 406/01001* (2013.01); *G01N 33/57446* (2013.01); *C12N 2310/14* (2013.01); *C12Q 2600/154* (2013.01); *C12Q 2600/158* (2013.01)

(56) References Cited

FOREIGN PATENT DOCUMENTS

| | | |
|---|---|---|
| WO | 2006105642 A1 | 10/2006 |
| WO | 2007014500 A1 | 2/2007 |
| WO | 2011073629 A2 | 6/2011 |

OTHER PUBLICATIONS

Seung-Hyun Hong et al., Upregulation of adenylate cyclase 3 (ADCY3) increases the tumorigenic potential of cells by activating the CREB pathway, Oncotarget, Oct. 2013, pp. 1791-1803, vol. 4, No. 10, Impact Journals, South Korea.

Extended European Search Report issued by European Patent Office in relation to PCT/KR2012006606 dated Feb. 23, 2016.

Lu, Le et al., Computational identification of potential microRNA network biomarkers for the progression stages of gastric cancer, International Journal of Data Mining and Bioinformatics, 2011, vol. 5, No. 5, pp. 519-531, See entire document.

Rui, Xianliang. Transcriptional Regulation of the Mouse Adenylyl Cyclase Type 4 (Adcy4) in Y1 Adrenocortical Tumor Cells, 2010, Degree of Doctor of Philosphy, Department of Pharmacology and Toxicology, University of Toronto See the entire document.

International Search Report filed in connection with PCT/KR2012/006606 dated May 14, 2013.

\* cited by examiner

SEQUENCE LISTING

<160> NUMBER OF SEQ ID NOS: 29

<210> SEQ ID NO 1
<211> LENGTH: 21
<212> TYPE: RNA
<213> ORGANISM: Artificial Sequence
<220> FEATURE:
<223> OTHER INFORMATION: siADCY3

```
<400> SEQUENCE: 1
auggagcacc agcuuccuca a                                              21

<210> SEQ ID NO 2
<211> LENGTH: 20
<212> TYPE: DNA
<213> ORGANISM: Artificial Sequence
<220> FEATURE:
<223> OTHER INFORMATION: forward primer for ADCY1

<400> SEQUENCE: 2
ccatccccaa cttcaatgac                                                20

<210> SEQ ID NO 3
<211> LENGTH: 20
<212> TYPE: DNA
<213> ORGANISM: Artificial Sequence
<220> FEATURE:
<223> OTHER INFORMATION: reverse primer for ADCY1

<400> SEQUENCE: 3
aggtgggagg agatggactt                                                20

<210> SEQ ID NO 4
<211> LENGTH: 20
<212> TYPE: DNA
<213> ORGANISM: Artificial Sequence
<220> FEATURE:
<223> OTHER INFORMATION: forward primer for ADCY2

<400> SEQUENCE: 4
ccatggtgga gtttgctttt                                                20

<210> SEQ ID NO 5
<211> LENGTH: 20
<212> TYPE: DNA
<213> ORGANISM: Artificial Sequence
<220> FEATURE:
<223> OTHER INFORMATION: reverse primer for ADCY2

<400> SEQUENCE: 5
tgacagtgtt gccccagata                                                20

<210> SEQ ID NO 6
<211> LENGTH: 20
<212> TYPE: DNA
<213> ORGANISM: Artificial Sequence
<220> FEATURE:
<223> OTHER INFORMATION: forward primer for ADCY3

<400> SEQUENCE: 6
gagtcacccc cgatgtcaac                                                20

<210> SEQ ID NO 7
<211> LENGTH: 20
<212> TYPE: DNA
<213> ORGANISM: Artificial Sequence
<220> FEATURE:
<223> OTHER INFORMATION: reverse primer for ADCY3

<400> SEQUENCE: 7
ttgccccaga tgtcgtagtg                                                20

<210> SEQ ID NO 8
<211> LENGTH: 20
```

-continued

```
<212> TYPE: DNA
<213> ORGANISM: Artificial Sequence
<220> FEATURE:
<223> OTHER INFORMATION: forward primer for ADCY4

<400> SEQUENCE: 8
ctctccaagc ccaagttcag                                           20

<210> SEQ ID NO 9
<211> LENGTH: 20
<212> TYPE: DNA
<213> ORGANISM: Artificial Sequence
<220> FEATURE:
<223> OTHER INFORMATION: reverse primer for ADCY4

<400> SEQUENCE: 9
actacgggtc catggttcaa                                           20

<210> SEQ ID NO 10
<211> LENGTH: 19
<212> TYPE: DNA
<213> ORGANISM: Artificial Sequence
<220> FEATURE:
<223> OTHER INFORMATION: forward primer for ADCY5

<400> SEQUENCE: 10
agtgtgtggc ggtcatgtt                                            19

<210> SEQ ID NO 11
<211> LENGTH: 20
<212> TYPE: DNA
<213> ORGANISM: Artificial Sequence
<220> FEATURE:
<223> OTHER INFORMATION: reverse primer for ADCY5

<400> SEQUENCE: 11
ctgccgatgg tcttgatctt                                           20

<210> SEQ ID NO 12
<211> LENGTH: 20
<212> TYPE: DNA
<213> ORGANISM: Artificial Sequence
<220> FEATURE:
<223> OTHER INFORMATION: forward primer for ADCY6

<400> SEQUENCE: 12
gaggcaaaca atgagggtgt                                           20

<210> SEQ ID NO 13
<211> LENGTH: 20
<212> TYPE: DNA
<213> ORGANISM: Artificial Sequence
<220> FEATURE:
<223> OTHER INFORMATION: reverse primer for ADCY6

<400> SEQUENCE: 13
tagtcagcca gggcagtgat                                           20

<210> SEQ ID NO 14
<211> LENGTH: 20
<212> TYPE: DNA
<213> ORGANISM: Artificial Sequence
<220> FEATURE:
<223> OTHER INFORMATION: forward primer for ADCY7

<400> SEQUENCE: 14
```
ggcgtggaga agatcaagac                                            20

<210> SEQ ID NO 15
<211> LENGTH: 20
<212> TYPE: DNA
<213> ORGANISM: Artificial Sequence
<220> FEATURE:
<223> OTHER INFORMATION: reverse primer for ADCY7

<400> SEQUENCE: 15
cggaaggagt tgaaggagtg                                            20

<210> SEQ ID NO 16
<211> LENGTH: 20
<212> TYPE: DNA
<213> ORGANISM: Artificial Sequence
<220> FEATURE:
<223> OTHER INFORMATION: forward primer for ADCY8

<400> SEQUENCE: 16
tgctgacttc gatgagttgc                                            20

<210> SEQ ID NO 17
<211> LENGTH: 20
<212> TYPE: DNA
<213> ORGANISM: Artificial Sequence
<220> FEATURE:
<223> OTHER INFORMATION: reverse primer for ADCY8

<400> SEQUENCE: 17
gtcagggcga gtgagaagtc                                            20

<210> SEQ ID NO 18
<211> LENGTH: 20
<212> TYPE: DNA
<213> ORGANISM: Artificial Sequence
<220> FEATURE:
<223> OTHER INFORMATION: forward primer for ADCY9

<400> SEQUENCE: 18
gctgctcctg ctctacgtct                                            20

<210> SEQ ID NO 19
<211> LENGTH: 20
<212> TYPE: DNA
<213> ORGANISM: Artificial Sequence
<220> FEATURE:
<223> OTHER INFORMATION: reverse primer for ADCY9

<400> SEQUENCE: 19
aggcggtagc tgacttcaaa                                            20

<210> SEQ ID NO 20
<211> LENGTH: 20
<212> TYPE: DNA
<213> ORGANISM: Artificial Sequence
<220> FEATURE:
<223> OTHER INFORMATION: forward primer for ADCY10

<400> SEQUENCE: 20
taggtacatg gaggggcaag                                            20

<210> SEQ ID NO 21
<211> LENGTH: 20
<212> TYPE: DNA
<213> ORGANISM: Artificial Sequence

```
<220> FEATURE:
<223> OTHER INFORMATION: reverse primer for ADCY10

<400> SEQUENCE: 21
gacgtaagcc atcaggtggt                                              20

<210> SEQ ID NO 22
<211> LENGTH: 25
<212> TYPE: DNA
<213> ORGANISM: Artificial Sequence
<220> FEATURE:
<223> OTHER INFORMATION: forward primer for ADCY3-HRM1

<400> SEQUENCE: 22
aaatagaagg aaggtttagg aattt                                        25

<210> SEQ ID NO 23
<211> LENGTH: 26
<212> TYPE: DNA
<213> ORGANISM: Artificial Sequence
<220> FEATURE:
<223> OTHER INFORMATION: reverse primer for ADCY3-HRM1

<400> SEQUENCE: 23
tcctatccct aacttataaa aaaacc                                       26

<210> SEQ ID NO 24
<211> LENGTH: 26
<212> TYPE: DNA
<213> ORGANISM: Artificial Sequence
<220> FEATURE:
<223> OTHER INFORMATION: forward primer for ADCY3-HRM2

<400> SEQUENCE: 24
ggttaggttt ttttataagt taggga                                       26

<210> SEQ ID NO 25
<211> LENGTH: 20
<212> TYPE: DNA
<213> ORGANISM: Artificial Sequence
<220> FEATURE:
<223> OTHER INFORMATION: reverse primer for ADCY3-HRM2

<400> SEQUENCE: 25
caaaaccttc cctaccaccc                                              20

<210> SEQ ID NO 26
<211> LENGTH: 25
<212> TYPE: DNA
<213> ORGANISM: Artificial Sequence
<220> FEATURE:
<223> OTHER INFORMATION: forward primer for ADCY3-HRM2

<400> SEQUENCE: 26
gttgggaggt ttttgtagta gagat                                        25

<210> SEQ ID NO 27
<211> LENGTH: 21
<212> TYPE: DNA
<213> ORGANISM: Artificial Sequence
<220> FEATURE:
<223> OTHER INFORMATION: reverse primer for ADCY3-HRM2

<400> SEQUENCE: 27
aaaaaaaacc acctccaaca a                                            21
```

```
<210> SEQ ID NO 28
<211> LENGTH: 25
<212> TYPE: DNA
<213> ORGANISM: Artificial Sequence
<220> FEATURE:
<223> OTHER INFORMATION: forward primer for ADCY3-BS

<400> SEQUENCE: 28
tttttaaggg atagtttgtg aattt                                              25

<210> SEQ ID NO 29
<211> LENGTH: 24
<212> TYPE: DNA
<213> ORGANISM: Artificial Sequence
<220> FEATURE:
<223> OTHER INFORMATION: reverse primer for ADCY3-BS

<400> SEQUENCE: 29
aaccctatcc tactcccaaa aaac                                               24
```

USE OF ADCY3 FOR DIAGNOSIS AND TREATMENT OF GASTRIC CANCER

CROSS-REFERENCE TO RELATED APPLICATIONS

This is a National Stage Application of International Patent Application No. PCT/KR2012/006606, filed Aug. 20, 2012, which claims the benefit of and priority to Korean Patent Application No. 10-2012-0078443, filed Jul. 18, 2012, the contents of which are incorporated fully by reference herein.

TECHNICAL FIELD

The present invention relates to the use of ADCY3 (Adenylate cyclase 3) in diagnosis and treatment of gastric cancer. More particularly, the present invention relates to a composition for detecting a gastric cancer marker, comprising an agent capable of assessing an mRNA, protein, or methylation level of ADCY3, a kit for diagnosing gastric cancer, comprising the composition, a method for diagnosing gastric cancer by treating a biological specimen with the agent to qualitatively and quantitatively a substance complimentary to the agent, a composition for treating and preventing gastric cancer, comprising an agent suppressing of ADCY3 polynucleotide or polypeptide, and a method for treating gastric cancer by administering the composition to a subject.

BACKGROUND ART

Gastric cancer is known to be the first or second largest cause to cancer-related death worldwide. Further, gastric cancer is one of the most common cancers, with a high incidence rate. According to the Cancer Facts & Figures reported by the Korean National Cancer Center, gastric cancer accounts for 15.4% of the total cancer cases of South Korea in 2009, ranking second for the entire population and first in men.

Gastric cancer exhibits various symptoms ranging from none at all to severe pain. Further, gastric cancer may cause only nonspecific symptoms, that is, symptoms that are specific not only to gastric cancer, but also to general digestive disorders. On the whole, gastric cancer produces no noticeable symptoms in its early stages. Even though present, the most common symptom of early gastric cancer is felt as light dyspepsia or epigastric discomfort by patients who are thus apt to regard it as insignificant, which contributes to the increased mortality of gastric cancer.

To date, the screening for and detection of gastric cancer resorts, for the most part, to physical means. First, gastric X-ray examination may be performed using a double contrast agent, with gastric compression, or on mucous membranes. Alternatively, gastroscopic examination may be the diagnostic method of choice. It allows the inside of the stomach to be visualized so as to detect those lesions which are too small for X-ray-based detection. Further, a questionable lesion can be biopsied via gastroscopy, thus increasing the diagnostic yield of gastric cancer. However, this physical examination is disadvantageous in terms of hygiene and in that the patient under examination suffers potential discomfort or pain. In recent years, active research has been directed toward the diagnosis of gastric cancer by measuring expression levels of gene markers specific for gastric cancers.

DISCLOSURE

Technical Problem

Leading to the present invention, intensive and thorough research into the development of a diagnostic method for gastric cancer that is accurate, with minimized pain and discomfort to patients, and into a therapeutic agent using the same, resulted in the finding that a specific gene and an expression product thereof are useful as a target of therapy as well as a diagnostic marker for gastric cancer.

Technical Solution

It is an object of the present invention to provide a composition for detecting a gastric cancer marker, comprising an agent capable of assessing an mRNA, protein, or methylation level of ADCY3 (adenylate cyclase 3).

It is another object of the present invention to provide a diagnostic kit for gastric cancer, comprising the composition.

It is a further object of the present invention to provide a method for diagnosing gastric cancer by treating a biological specimen with an agent capable for assessing an mRNA or protein expression level of ADCY3, detecting the binding of the agent to a polynucleotide or protein complimentary to the agent, and comparing the detection level between a subject and a normal control.

It is a still further object of the present invention to provide a composition for treating and preventing gastric cancer, comprising an oligonucleotide suppressive of the expression of ADCY3 mRNA, or an antibody inhibitory of the activity of ADCY3, or an antigen-binding fragment thereof.

It is still another object of the present invention to provide a method for treating gastric cancer, comprising administering the composition to a subject in need thereof.

It is yet another object of the present invention to provide a method for screening a therapeutic agent of gastric cancer, comprising treating a cell expressing an ADCY3 with a therapeutic agent candidate, and measuring an expression level of the ADCY3 polypeptide.

Advantageous Effects

Showing high diagnostic sensitivity and specificity for gastric cancer, the use of ADCY3 as a diagnosis marker for gastric cancer in accordance with the present invention can make great contribution to a reduction in the mortality of gastric cancer. Further, an agent capable of controlling the expression of ADCY3 in accordance with the present invention can be applied to the prophylaxis and therapy of gastric cancer.

DESCRIPTION OF DRAWINGS

FIG. 1 shows ADCY3 mRNA expression levels in gastric cancer cells and tissues.

DESCRIPTION OF EMBODIMENTS

In accordance with an aspect thereof, the present invention addresses a composition for detecting a gastric cancer marker, comprising an agent capable of assessing an mRNA or protein expression level of ADCY3.

As used herein, the term "ADCY3", stands for adenylate cyclase 3, which is a transmembrane enzyme of about 128 kDa belonging to the adenylate cyclase family and catalyzes the formation of the secondary messenger cAMP.

The ADCY3 protein, as its name implies, is type 3 of the adenylate cyclase family consisting of 10 members. Some of the family members are known to be upregulated in some cancer tissues, but nowhere has the gastric cancer-specific upregulation of ADCY3 been mentioned in any document prior to the present disclosure. Information on ADCY3 protein and mRNA can be obtained from known databases, for example, from the GenBank of NCBI, but is not limited thereto. Information of amino acid sequence for the above protein can be NCBI GenBank Accession No. NP_004027, but is not limited thereto.

Figure 1A:
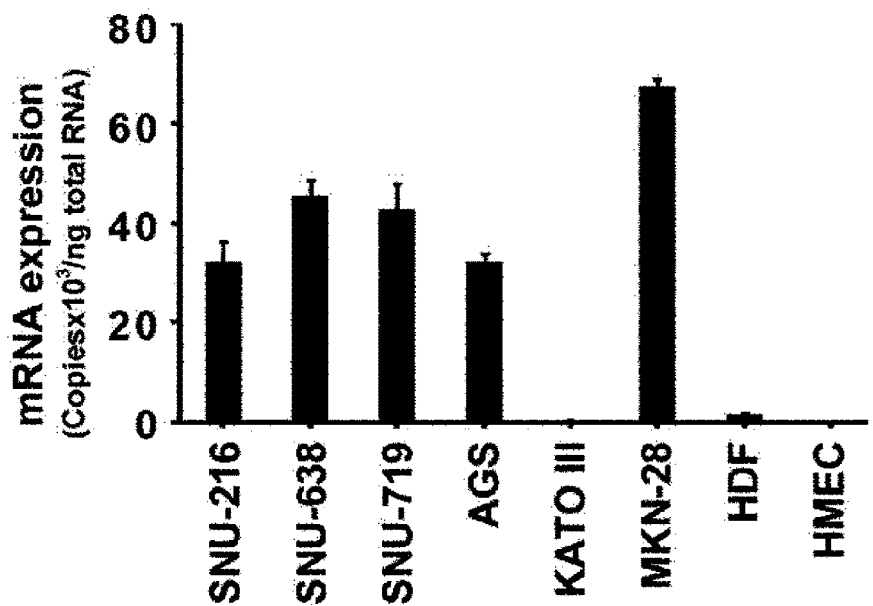
FIG. 1A shows the quantification of ADCY3 mRNA in gastric cancer cells and normal human cells.
Figure 1B:
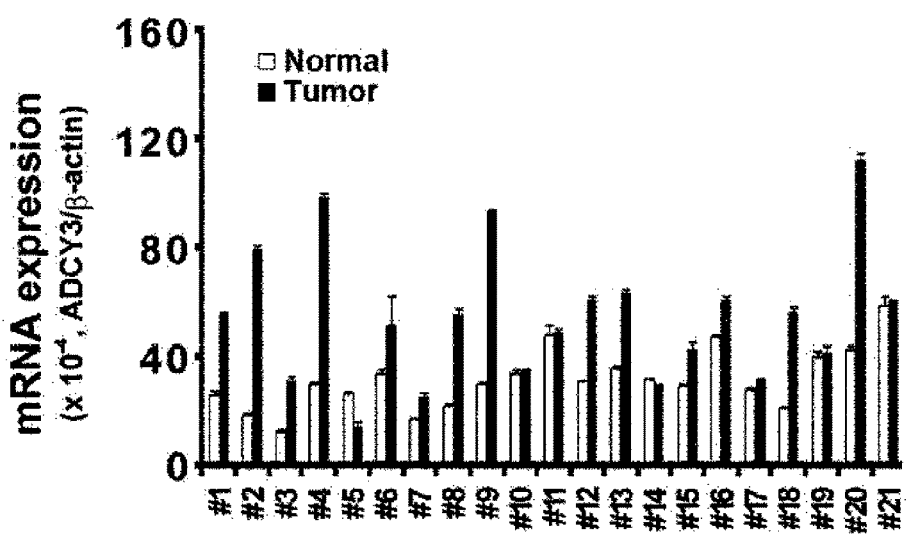
FIG. 1B shows the relative quantification of ADCY3 mRNA in gastric cancer tissues and normal tissues.

In the present invention, the gastric cancer-specific upregulation of ADCY3 is first revealed. In one embodiment of the present invention, ADCY3 expression levels were found to be significantly higher in six human gastric cancer cell lines (SNU-216, SNU-638, SNU-719, AGS, KATO III, and MKN28) than in normal cell lines (HDF, and HMEC) (FIG. 1A). Further, higher ADCY3 expression levels were detected in gastric cancer tissues, compared to adjacent normal tissues (FIG. 1B). Therefore, ADCY3 can be applicable as a diagnosis marker specific for gastric cancer.

The term "marker or diagnosis marker", as used herein, means a substance capable of distinguishing gastric cancer cells or subjects from normal cells or subjects, and may include an organic biomolecule such as a polypeptide, a protein, a polynucleotide (e.g., mRNA etc.), a lipid, a glycolipid, a glycoprotein, and a sugar (monosaccharide, disaccharide, oligosaccharide etc.) that is expressed at a higher or lower level in gastric cancer cells or subjects, as compared to its level in normal cells or subjects. With respect to the objects of the present invention, the diagnosis marker for gastric cancer of the present invention is an ADCY polypeptide or a polynucleotide coding for the same, which is highly expressed in gastric cancer cells, as compared to normal cells or tissues.

The term "assessing an mRNA expression level", as used herein, is a process of examining mRNA presence and expression level of a gastric cancer marker gene in a biological sample for the diagnosis of gastric cancer, and can be performed by measuring an amount of the mRNA. In this regard, an analysis method may include RT-PCR, competitive RT-PCR, real time RT-PCR, RNase protection assay (RPA), Northern blotting, and DNA chip, but are not limited thereto.

The term "assessing a protein expression level", as used herein, is a process of examining the presence and expression level of a protein expressed from a gastric cancer marker gene in a biological sample for the diagnosis of gastric cancer, and can be performed by measuring an amount of the protein using an antibody specific to the protein encoded by the gene. In this regard, an analysis method may include Western blotting, ELISA (enzyme linked immunosorbent assay), RIA (radioimmunoassay), radioimmunodiffusion, ouchterlony immunodiffusion, rocket immunoelectrophoresis, immunohistostaining, immunoprecipitation assay, complement fixation assay, FACS, and protein chip, but are not limited thereto.

The agent capable of assessing an mRNA expression level is preferably a pair of primers, a probe, or an anti-sense nucleotide for the ADCY3 polynucleotide or a fragment thereof in accordance with the present invention. Based on a sequence of the polynucleotide of the present invention, those skilled in the art are able to readily design the primer pair, probe or antisense nucleotide sequence.

The term "primer", as used herein, means a short nucleic acid strand having a free 3' hydroxyl group, which is able to form a base pair with a complementary template, and functions as a starting point for amplifying the template. The primer can initiate DNA synthesis in the presence of a regent for polymerization in a suitable buffer solution, at a suitable temperature (DNA polymerase, or reverse transcriptase) and four different deoxynucleoside triphosphates. In the present invention, PCR is performed using sense and antisense primers of UQCRH polynucleotide to identify the production of a desired product, thereby diagnosing liver cancer. PCR conditions and length of sense and antisense primers can be modified on the basis of the methods known in the art.

By the term "primer" is, as used herein, meant a short nucleic acid strand having a free 3'-hydroxyl group that is able to form a base pair with a complementary template and which functions as a starting point for amplifying the template. A primer can be used to initiate DNA synthesis in the presence of a regent for polymerization in a suitable buffer solution at a suitable temperature (DNA polymerase, or reverse transcriptase), and of four different deoxynucleoside triphosphates. In the present invention, PCR may be performed using sense and antisense primers of ADCY3 polynucleotide to identify the production of a desired product, thereby diagnosing gastric cancer. PCR conditions, and lengths of sense and antisense primers can be modified on the basis of the methods known in the art.

As used herein, the term "probe" refers to a fragment of nucleic acid such as an RNA or DNA that is ones to hundreds of base pairs capable of specifically binding to mRNA and which may be labeled to identify the presence of specific mRNA. A probe may be prepared in a form of oligonucleotide probe, single stranded DNA probe, double stranded DNA probe, RNA probe or the like. In the present invention, the onset of gastric cancer can be diagnosed from results of hybridization between ADCY3 polynucleotide and its complementary probe. Modification may be made of probe selection and hybridization condition, based on methods known in the art.

The primer or probe of the present invention can be chemically synthesized using a phosphoramidite solid support method or other well-known methods. Modifications may also be made on the nucleotide sequence using various methods known in the art. Non-limiting examples of such modifications include methylation, capping, substitution with one or more homologues of natural nucleotide, and modification between nucleotides, for example, modification into an uncharged linker (e.g., methyl phosphonate, phosphotriester, phosphoroamidate, and carbamate) or charged linker (e.g., phosphorothioate, phosphorodithioate).

Preferably, the primer or probe contains 8 or more nucleotides. Hybridization may be achieved by exposing or contacting the primer or probe to the ADCY3 polynucleotide of the present invention. Preferably, these sequences are hybridized with each other under such a stringent condition as to minimize non-specific pairings. In order to detect sequences which share 80% to 90% homology with the ADCY3 polynucleotide of the present invention, for example, a hybridization condition may include hybridizing overnight at 42° C. in a buffer containing 0.25M $Na_2HPO_4$, pH 7.2, 6.5% SDS, and 10% dextran sulfate and finally washing at 55° C. with a solution containing 0.1×SSC and 0.1% SDS. A stringent condition suitable for detecting a sequence which shares 90% homology with the ADCY3 polynucleotide of the present invention comprises hybridizing overnight at 65° C. in 0.25M $Na_2HPO_4$, pH 7.2, 6.5% SDS, 10% dextran sulfate, and finally washing at 60° C. with a solution containing 0.1×SSC and 0.1% SDS.

In accordance with an embodiment of the present invention, the agent for assessing an expression level of ADCY3 protein (hereinafter, used interchangeably with "ADCY3 polypeptide") is preferably an antibody. The term "antibody", as used herein, refers to a specific protein molecule that indicates an antigenic region. With respect to the objects of the present invention, the antibody binds specifically to the marker of the present invention, that is, an ADCY3 polypeptide. This antibody can be produced from a protein that the marker gene cloned typically into an expression vector encodes, using a conventional method. Also, partial peptides producible from the protein encoded by the marker gene fall within the scope of the antibody. For functioning as an antibody, the partial peptide is required to contain at least 7 amino acid residues, preferably 9 or more amino acid residues, and more preferably 12 or more amino acid residues. No particular limitations are imparted to the form of the antibodies of the present invention. Among them are polyclonal antibodies, monoclonal antibodies and fragments thereof that contain a paratope, and all immunoglobulin antibodies. Further, special antibodies such as humanized antibodies are also within the scope of the present invention. Consequently, as long as it may be produced using a method known in the art, any antibody against the ADCY3 protein of the present invention can be used in the present invention.

In addition, the antibodies of the present invention that are used for detecting the diagnosis marker of gastric cancer include functional fragments of antibody molecules as well as complete forms having two full-length light chains and two full-length heavy chains. The functional fragments of antibody molecules refer to fragments retaining at least an antigen-binding function, and include Fab, F(ab'), F(ab')2, Fv and the like.

The composition for detecting a gastric cancer marker in accordance with the present invention may an agent capable of assessing a methylation level of the ADCY3 gene. Studies on the role of DNA methylation in cancer-related gene expression has recently been conducted, revealing that the mRNA expression of cancer gene is regulated depending on DNA methylation. Accordingly, the methylation level of the ADCY3 gene is measured in the present invention to diagnose gastric cancer if a low methylation level is detected.

As used herein, the term "methylation" means the addition of a methyl group to a base to change the expression pattern of the gene. For the purpose of the present invention, methylation occurs on the ADCY3 gene. In detail, the methylation of the present invention is directed to methylation on cytosine residues of CpG islands wherein C and G bases exist repetitively along the length of ADCY3 gene. In the context of the methylation, the binding of transcription factors to a gene is blocked to inhibit the expression of the gene.

The term "assessing a methylation level" means the analysis of a nucleic acid sequence for the degree of methylation. For the purpose of the present invention, it is very important to assess the methylation level of the ADCY3 gene. Any method that is known in the art to measure a methylation level may be employed without limitations, and may include Goldengate Methylation Cancer Panel I microarray, EpiTYPER™ assay, methylation-specific polymerase chain reaction (hereinafter referred to as "MSP"), and automatic base sequencing.

In one embodiment of the present invention, gastric cancer cell lines overexpressing ADCY3 were discovered to exhibit hypomethylation on the ADCY3 gene (FIG. 5C), and thus to regulate ADCY3 expression depending on the degree of DNA methylation of CpG islands in the promoter region. Consequently, assessment of the methylation level of the ADCY3 gene can be applicable as a diagnosis marker of gastric cancer.

The term "gastric cancer", as used herein, is a generic term of carcinoma (malignant tumor) developed in the stomach. There are various malignant tumors of the stomach, including gastric adenocarcinoma, lymphoma, gastric submucosal tumor, and leiomyosarcoma, with gastric adenocarcinoma accounting for 98% of the total gastric cancer cases. Thus, gastric cancer may be preferably gastric adenocarcinoma. Symptoms of gastric cancer include upper abdominal discomfort, upper abdominal pain, dyspepsia, abdominal distension, and loss of appetite. These symptoms, however, cannot be used solely as diagnostic indications, but radioactive or gastroscopic examination is a useful diagnosis means of gastric cancer, with the final diagnosis made by biopsy. In the present invention, these cumbersome and complex diagnosis methods are not employed. Instead, gastric cancer can be simply diagnosed by measuring the level of ADCY3, which is now found to be a gastric cancer marker.

Figure 2:
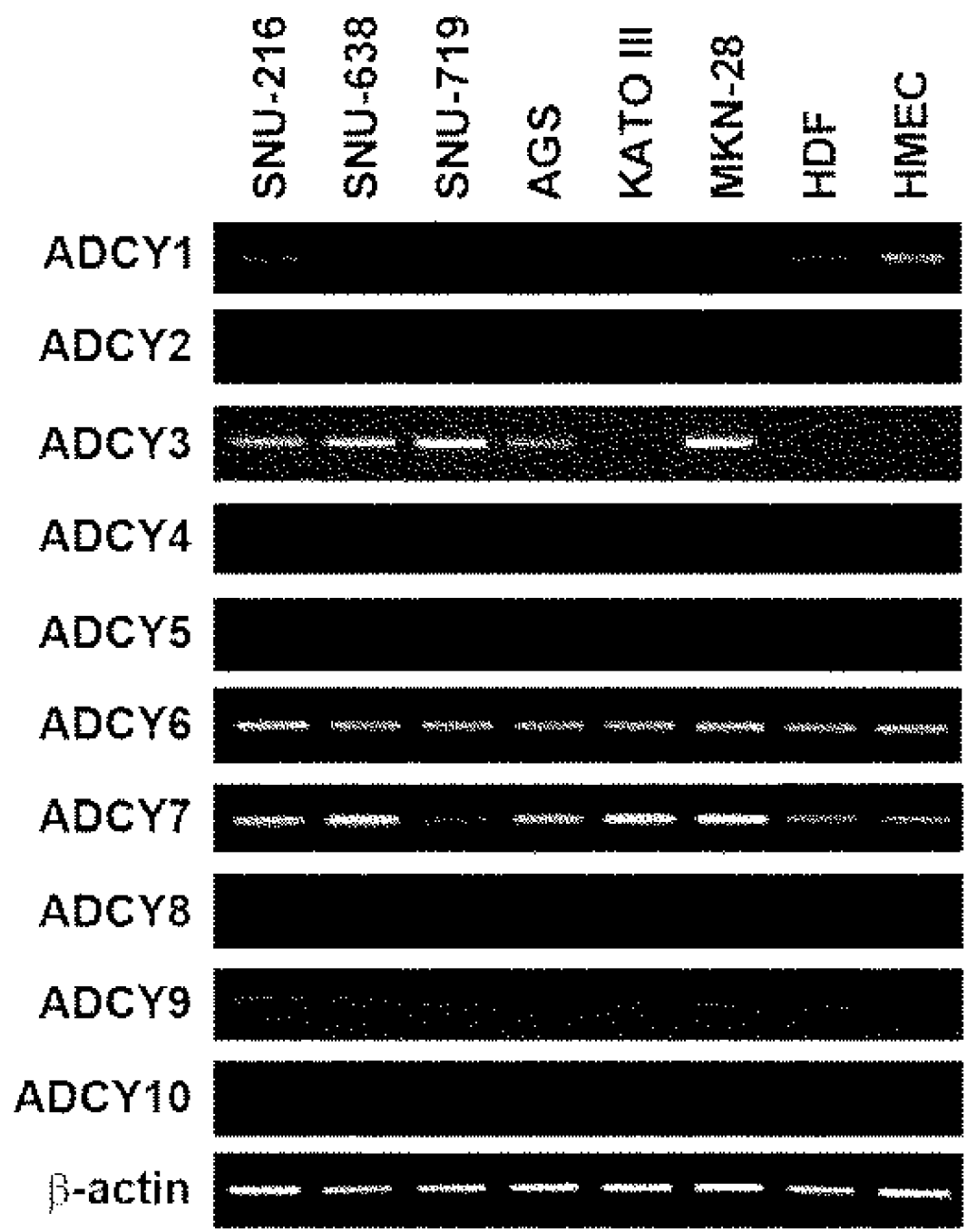
FIG. 2 shows the expression of ADCY family members in six gastric cancer cell lines (SNU-216, SNU-638, SNU-719, AGS, KATOIII, and MKN28) and two normal cell lines (HDF and HMEC), as analyzed by RT-PCR.

In one preferred embodiment of the present invention, only ADCY3 shows a gastric cancer-specific expression pattern, but the other members of the ADCY family do not (FIG. 2). That is, all the ADCY family members are not be expressed in gastric cancer cells, but ADCY3 alone is expressed specifically for gastric cancer. This result suggests the applicability of ADCY3 as a gastric cancer-specific marker. Therefore, the composition for detecting a gastric cancer maker, comprising an agent capable of assessing an mRNA or protein expression level of ADCY3 can be used as a marker for the diagnosis of gastric cancer.

In accordance with another aspect thereof, the present invention provides a gastric cancer diagnosis kit that comprises an agent for assessing an mRNA or protein expression level of ADCY3

The term "diagnosis", in the context of the present invention, refers to a process of determining the presence or absence of the ADCY3 polypeptide or polynucleotide of the present invention in a biological specimen or a tissue sample so as to identify the existence or characteristics of a disease related to the expression of the gene.

The detection of the cancer marker may be accomplished by determining the expression level of the ADCY3 polypeptide or a polynucleotide encoding it using the kit of the present invention. The kit of the present invention may comprise a primer or probe for assessing the expression level of the cancer diagnosis marker, an antibody selectively recognizing the cancer marker or its fragments retaining an antigen-binding function, and/or one or more agents or compositions suitable for the analysis of the polypeptide or polynucleotide. For example, the diagnosis kit for the quantitative analysis of the polynucleotide or gene of the present invention may comprise at least one oligonucleotide specifically binding to a polynucleotide coding for the ADCY3 polypeptide. In a preferable embodiment, the diagnosis kit of the present invention is characterized by including essential elements required for performing RT-PCR. An RT-PCR kit includes a pair of primers specific for the polnucleotide of ADCY3 or a part of the sequence, reverse transcriptase, Taq polymerase, PCR primers, and dNTP. As long as it takes advantage of analysis methods known in the context of "assessing an mRNA expression level", any kit may be employed without limitations.

In another preferable embodiment, the gastric cancer diagnosis kit of the present invention may comprise an antibody specifically binding to the ADCY3 protein of the present invention. As long as it takes advantage of analysis methods known in the context of "assessment of protein expression level", any kit may be employed without limitations. Preferable is an ELISA kit or a protein chip kit.

The assessment of protein expression level using an antibody is based on the formation of an antigen-antibody complex between the ADCY3 protein and an antibody thereto. Leading to determining the protein expression level, the amount of the antigen-antibody can be measured using various methods.

As used herein, the term "antigen-antibody complex" is intended to refer to binding products of a cancer marker protein to an antibody specific thereto. The antigen-antibody complex thus formed may be quantitatively determined by measuring the signal size of a detection label.

For instance, gastric cancer can be diagnosed by determining a significant increase in ADCY3 protein expression level in a suspected subject from the comparison of the amount of antibody-antigen complex between the suspected subject and a normal control. In this regard, a sample from a subject with suspected gastric cancer is treated with an antibody specific for the inventive ADCY3 protein to form an antigen-antibody complex that can be quantitatively analyzed using a kit on the basis of an ELISA assay, an RIA assay, a sandwich ELISA assay, a Western blotting assay, a radioimmunodiffusion assay, an ouchterlony immunodiffusion assay, a rocket immunoelectrophoresis assay, an immunohistostaining assay, an immunoprecipitation assay, a complement fixation assay, FACS, a protein chip assay or an immunodot assay. Comparison of the analysis data with those of a normal subject allows the diagnosis of cancer in connection with an increase in ADCY3 protein expression.

In accordance with a further aspect thereof, the present invention pertains to a method for diagnosing gastric cancer, comprising treating a biological specimen with the agent for assessing an mRNA or protein expression level of ADCY3, detecting a complex of the agent with a polynucleotide or protein complementary thereto, and quantitatively comparing the amount of the complex between a subject and a normal control.

In the diagnosis method of gastric cancer, the onset of gastric cancer can be determined by measuring ADCY3, identified as a gastric cancer marker in the present invention, at an mRNA or the protein level.

As used therein, the term "biological specimen" is intended to refer to a sample from which a gene or protein expression level of ADCY3 can be measured. Examples of the biological specimen useful in the present invention include tissues, cells, whole blood, serum, plasma, saliva, sputum, cerebrospinal fluid and urine, but are not limited thereto. mRNA or protein isolation from a biological specimen may be achieved using a well-known method.

In an embodiment of the method according to the present invention, a gene expression level in a subject with suspected cancer can be compared to that in a normal control to diagnose cancer incidence in the subject. In detail, a biological specimen from a subject with suspected cancer is measured for the expression level of the marker of the present invention. This level is compared with that measured in a biological specimen from a normal control. When the expression level of the marker of the present invention is higher in the subject than in the normal control, the subject may be determined to be affected by gastric cancer.

In the case where a polynuceotide coding for the ADCY3 polypeptide of the present invention is used as a marker, the method comprises (a) providing a biological specimen; (b) treating the biological specimen with an agent for measuring an expression level of ADCY3; (c) detecting the agent and/or a binding product of the agent to a polynucleotide complementary to the agent; and (d) quantitatively comparing the binding product between a subject and a normal control. In the case where the ADCY3 polypeptide of the present invention is used as a marker, the method comprises (a) providing a biological specimen; (b) treating the biological specimen with an antibody specific for the ADCY3 protein; (c) detecting an antigen-antibody complex; and (d) quantitatively comparing the complex between a subject and a normal control.

In accordance with still a further aspect thereof, the present invention pertains to a composition for the treatment and prevention of cancer, comprising as an active ingredient an oligonucleotide inhibitory of the expression of an ADCY3 mRNA or an antibody inhibiting the activity of ADCY3 polypeptide or an antigen-binding fragment thereof.

In a preferred embodiment of this aspect, the composition of the present invention may include a substance inhibiting the expression of ADCY3 mRNA of the present invention. The ADCY3 mRNA expression inhibitor substance may be selected from the group consisting of siRNA, shRNA, an aptamer and an antisense oligonucleotide.

As used herein, the term "siRNA (small interfering RNA)" is intended to refer to a small nucleic acid molecule of about nucleotides, which mediates RNA interference or gene silencing. When siRNA is introduced into a cell, it is recognized by dicer to degrade the gene encoding the ADCY3m, resulting in the specific knockdown of an ADCY3 gene. The siRNA may preferably have the nucleotide sequence of SEQ ID NO: 1, but is not limited thereto.

The term "shRNA" refers to a short hairpin RNA in which sense and antisense sequences of a siRNA target sequence are separated by a loop structure of 5 to 9 bases.

As used herein, the term "aptamer", meaning a small RNA fragment, refers to an oligoribonucleic acid molecule which is 20 to 60 nt long. It has various three-dimensional structures depending on sequences and binds to a specific target molecule to effectively regulate the function of the target molecule.

Recently, the phenomenon of RNA interference (RNAi) has been studied for application to a method for controlling protein expression at the gene level. Typically, siRNA has been shown to inhibit protein expression by binding specifically to mRNA, having a sequence complementary to a target gene.

As used herein, the term "antisense" is intended to refer to an oligomer having a sequence of nucleotide bases and a subunit-to-subunit backbone that allows the antisense oligomer to hybridize with a target sequence in RNA by Watson-Crick base pairing to form an RNA:oligomer heteroduplex within the target sequence, typically with mRNA. The oligomer may have exact sequence complementarity to the target sequence, or near complementarity thereto. These antisense oligomers may block or inhibit the translation of the mRNA, and/or modify the processing of mRNA to produce a splice variant of the mRNA. Thus, the antisense oligomer of the present invention is an antisense oligomer complementary to a polynucleotide coding the ADCY3 polypeptide.

In a preferred embodiment thereof, the present invention provides a composition suppressive of the growth or metastasis of cancer, comprising a substance inhibiting the activity or expression of the ADCY3 protein. Preferably, the activity-inhibiting substance is an antibody that specifically recognizes an ADCY3 protein. The antibody includes all monoclonal antibodies and chimeric antibodies, humanized antibodies, and human antibodies thereof. As long as they have the binding property of specifically recognizing ADCY3, the antibodies include complete forms having two full-length light chains and two full-length heavy chains, or may be in the form of functional fragments of antibody molecules. As used herein, the term "functional fragments of antibody molecules" is intended to refer to fragments retaining at least an antigen-binding function, which are exemplified by Fab, F(ab'), F(ab')$_2$ and Fv.

Figure 3A:
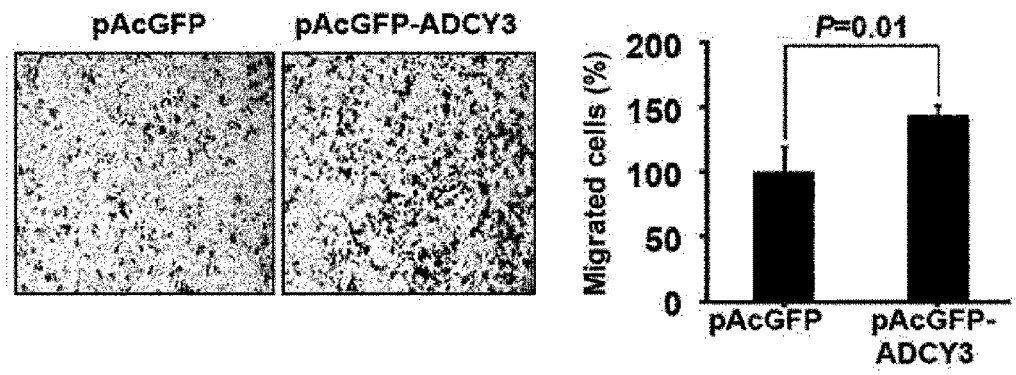
FIG. 3 shows effects of ADCY3 expression on tumorigenesis-related cell behaviors including migration, (A), invasiveness (B), and clonogenecity (E) HEK293 cells, and effects of siRNA on ADCY3 silencing in SNU216 gastric cancer cell line in terms of downregulation of ADCY3 expression (D), cell migration (E), invasiveness (F), and clonogenecity (G)
Figure 3B:
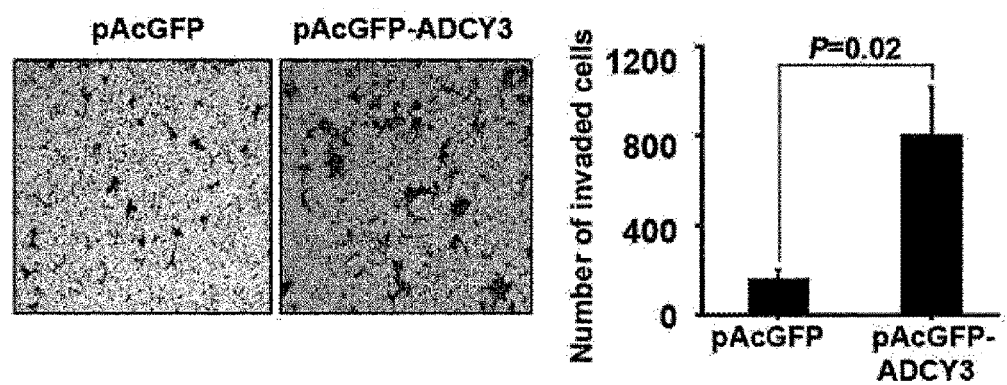
Figure 3C:
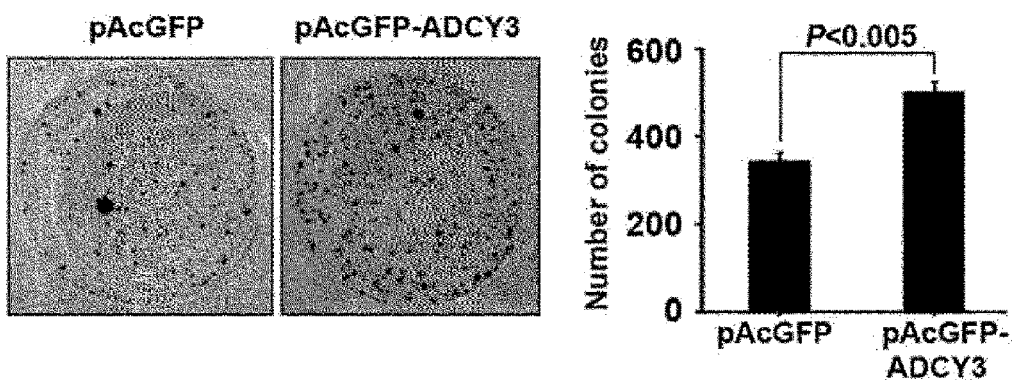
Figure 3D:
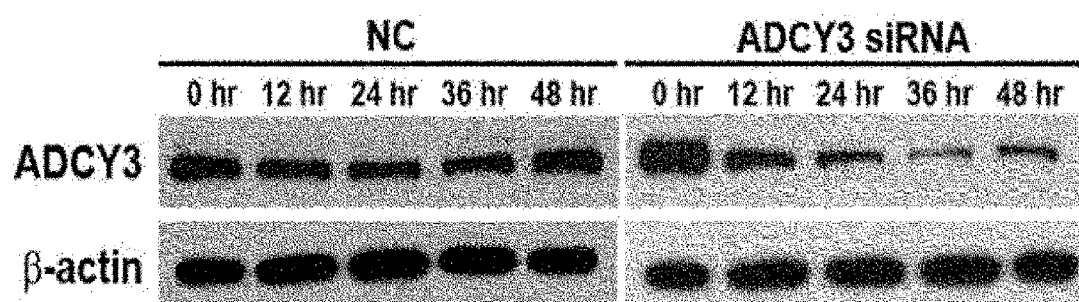
Figure 3E:
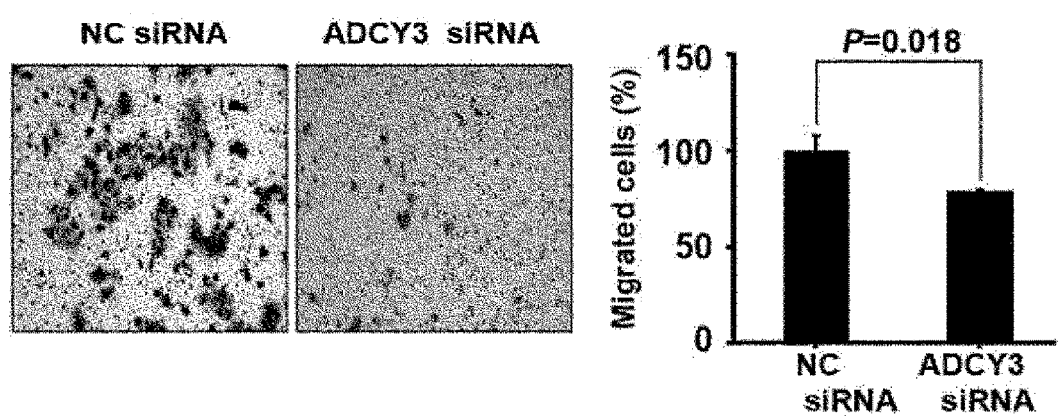

In one preferred embodiment of the present invention, the overexpression of ADCY3 is found to increase cells in migration, invasiveness and clonogenicity, demonstrating that ADCY3 is involved in tumorigenesis (FIGS. 3A to 3C). Downregulation of ADCY3 with specific siRNA results in decreasing cell migration, invasiveness and clonogenecity, revealing that the tumorigenesis-related effects can be attenuated by suppressing ADCY3 (FIGS. 3D to 3G).

Therefore, the therapeutic effect on gastric cancer in accordance with the present invention can be achieved by suppressing the metastasis of gastric cancer. On the whole, malignant tumor such as gastric cancer grows rapidly and is apt to invade adjacent tissues, with concomitant metastasis to aggravation. The composition suppressive of the expression and activity of ADCY3 in accordance with the present invention inhibits the metastasis of gastric cancer by reducing migration, invasiveness and clonogenecity, thereby exerting therapeutic effects on gastric cancer.

Preferably, the composition according to the present invention may include an acceptable carrier appropriate to the administration mode thereof.

The active ingredient may be combined with pharmaceutically acceptable vehicles, excipients, or additives. Examples of the pharmaceutically acceptable carriers useful in the present invention include physiological saline, sterile water, Ringer's solution, buffered saline, dextrose solution, maltodextrin solution, glycerol, ethanol, and liposomes. They may be used alone or in combination. If necessary, the composition may further comprise other typical additives such as antioxidants, buffers, etc. Depending on administration mode, the composition may be formulated with a diluent, a dispersant, a surfactant, a binder and a lubricant into an injection dosage form such as aqueous solution, suspension, emulsion, etc. or an oral dosage form such as pill, capsule, granule, tablet, etc. When conjugated with the carrier, an antibody or ligand specific for target organs or tissues may direct the active ingredient toward the organs or tissues. Typical vehicles, excipients and additives known in the art may be used in the present invention. The present invention is not limited to the examples of vehicles, excipients and additives.

The composition or formulation may be administered in a therapeutically effective amount to subjects through a suitable route according to purpose or necessity. The pharmaceutical composition may be administered orally, parenterally, subcutaneously, intraperitoneally, or intranasally. For local immunosuppressive therapy, the composition may, if desired, be administered using a suitable method, including intralesional administration. Parenteral injections include intramuscular, intravenous, intraarterial, intraperitoneal and subcutaneous routes. The therapeutically effective amount of the composition comprising the antisense oligonucleotide, siRNA or shRNA may vary depending on various factors well known in the medical art, including the kind and degree of the response to be achieved, routes of administration, sex, state of health, diet, the patient's age and body weight, and severity of disease.

In accordance with a yet further aspect thereof, the present invention addresses a method for treating gastric cancer, comprising administering the composition to a subject. The composition administered to a subject is as defined above, and may be a composition for the treatment and prevention of gastric cancer, comprising an oligonucleotide suppressive of the expression of ADCY3 mRNA, or an antibody or an antigen-binding fragment thereof inhibiting the activity of ADCY3 protein.

As mentioned above, the composition to be administered to the subject may include an acceptable carrier appropriate to the administration mode thereof. Administration modes, routes, and doses modes may be properly determined in consideration of various factors, as mentioned above.

In accordance with yet another aspect thereof, the present invention is directed to a method for screening a curative agent for gastric cancer, comprising treating a cell expressing an ADCY3 polypeptide with a candidate compound, and measuring an ADCY3 polypeptide expression level in the cell.

In the screening method of the present invention, the candidate compound, if inducing an increase in ADCY3 expression level, is determined as being oncogenic. When the ADCY3 expression level is reduced thereby, the candidate compound is determined as a possible therapeutic agent for cancer. According to the screening method, the activity of the candidate can be easily determined by the ADCY3 expression level.

In accordance with a yet still further aspect thereof, the present invention addresses the use of an agent for assessing an mRNA, protein, or methylation level of ADCY, or a composition comprising the same in detecting a gastric cancer marker. ADCY3 and the composition are as defined above, and they are applicable to the diagnosis of gastric cancer.

In accordance with yet still another aspect thereof, the present invention addresses the use of an oligonucleotide suppressive of the expression of ADCY3 mRNA, an antibody or an antigen-binding fragment thereof suppressive of the activity of ADCY protein, or a composition comprising the oligonucleotide or antibody or antigen-binding fragment thereof. In this regard, ADCY3 and the composition are as defined above, and they are applicable to the diagnosis of gastric cancer.

MODE FOR INVENTION

A better understanding of the present invention may be obtained through the following examples which are set forth to illustrate, but are not to be construed as limiting the present invention.

Example 1: Preparation of Cell and Tissue Samples

Human cancer cell lines (SNU-216, SNU-638, SNU-719-KCLB, Seuol, Korea; AGS, KATOIII, MKN28, HCT-116, SNU-81, SK-BT-3, Manassas, USA), human dermal fibroblast (HDF, obtained from ATCC), and HEK293 cells were cultured in growth media (Cellgro, USA) supplemented with 10% (v/v) fetal bovine serum and 1× penicillin-streptomycin (Invitrogen, USA). Human mammary epithelial cells (HMEC; Lonza, Switzerland) were cultured according to the manufacturer's instructions. Normal and gastric cancer tissue samples (Table 1) were obtained in accordance with the principles of the Declaration of Helsinki and were approved by the institutional review board of the National Cancer Center, Korea for human subject studies (Approval No. NCCNCS-08-127).

TABLE 1

|   |   |   | No. of patients (%) |
|---|---|---|---|
| A. Patient group for microarray (n = 27) | | | |
| No. of patients | | Male | 20 (74.1%) |
|  |  | Female | 7 (25.9%) |
|  |  | Total | 27 |
| Age at diagnosis (years) |  | Range | 44-78 |
|  |  | Mean ± SD | 59.7 ± 11.2 |
| Disease stage | T clasification | T1 | 17 (63.0%) |
|  |  | T2 | 10 (37.0%) |
|  | N classification | N0 | 13 (48.1%) |
|  |  | N1 | 10 (37.0%) |
|  |  | N2 | 2 (7.4%) |
|  |  | N3 | 2 (7.4%) |
| B. Patient group for RT-PCR analysis (n = 21) | | | |
| No. of patients |  | Male | 14 (66.7%) |
|  |  | Female | 7 (33.3%) |
|  |  | Total | 21 |
| Age at diagnosis (years) |  | Range | 44-78 |
|  |  | Mean ± SD | 63.2 ± 10.7 |
| Disease stage | T classification | T1 | 12 (57.1%) |
|  |  | T2 | 9 (42.9%) |
|  | N classification | N0 | 9 (42.9%) |
|  |  | N1 | 7 (33.3%) |
|  |  | N2 | 3 (14.3%) |
|  |  | N3 | 2 (9.5%) |

Example 2: Detection of mRNA Expression by RT-PCR, qRT-PCR and Northern Blotting cDNA was synthesized from 2 μg of random primed total RNA from cultured cells using SuperScript™ III First-Strand Synthesis kit (Invitrogen). Also, human cDNA was obtained from the Human Multiple Tissue cDNA panel I (Clontech, USA) and Human Digestive System MTC panel (Clontech, USA). Primers for RT-PCR or qRT-PCR were designed using the internet site "Primer3 frodo.wi.mit.edu/primer3" to span two consecutive exons of each ADCY gene (Table 2).

TABLE 2

| Primer Name | Sequence (5'→3') | Sequence List |
|---|---|---|
| ADCY1-F | CCATCCCCAACTTCAATGAC | SEQ. ID. No. 2 |
| ADCY1-R | AGGTGGGAGGAGATGGACTT | SEQ. ID. No. 3 |
| ADCY2-F | CCATGGTGGAGTTTGCTTTT | SEQ. ID. No. 4 |
| ADCY2-R | TGACAGTGTTGCCCCAGATA | SEQ. ID. No. 5 |
| ADCY3-F | GAGTCACCCCGATGTCAAC | SEQ. ID. No. 6 |
| ADCY3-R | TTGCCCCAGATGTCGTAGTG | SEQ. ID. No. 7 |
| ADCY4-F | CTCTCCAAGCCCAAGTTCAG | SEQ. ID. No. 8 |
| ADCY4-R | ACTACGGGTCCATGGTTCAA | SEQ. ID. No. 9 |
| ADCY5-F | AGTGTGTGGCGGTCATGTT | SEQ. ID. No. 10 |
| ADCY5-R | CTGCCGATGGTCTTGATCTT | SEQ. ID. No. 11 |
| ADCY6-F | GAGGCAAACAATGAGGGTGT | SEQ. ID. No. 12 |
| ADCY6-R | TAGTCAGCCAGGGCAGTGAT | SEQ. ID. No. 13 |
| ADCY7-F | GGCGTGGAGAAGATCAAGAC | SEQ. ID. No. 14 |
| ADCY7-R | CGGAAGGAGTTGAAGGAGTG | SEQ. ID. No. 15 |
| ADCY8-F | TGCTGACTTCGATGAGTTGC | SEQ. ID. No. 16 |
| ADCY8-R | GTCAGGGCGAGTGAGAAGTC | SEQ. ID. No. 17 |
| ADCY9-F | GCTGCTCCTGCTCTACGTCT | SEQ. ID. No. 18 |
| ADCY9-R | AGGCGGTAGCTGACTTCAAA | SEQ. ID. No. 19 |
| ADCY10-F | TAGGTACATGGAGGGGCAAG | SEQ. ID. No. 20 |
| ADCY10-R | GACGTAAGCCATCAGGTGGT | SEQ. ID. No. 21 | qRT-PCR reactions were performed using a LightCycler 480 (Roche Applied Science, UK) and ABI 7500 Fast Real-Time PCR system (Applied Biosystems). Results were quantified either by using β-actin for normalization (relative quantification), or by standard curve-based absolute quantification.

For Northern blotting, total RNA (20 μg/lane) was UV-fixed onto Hybond-N$^+$ membrane (Amersham Bioscience, UK), and incubated overnight at 42° C. in $^{32}$P-labeled probe-containing ULTRAhyb solution (Ambion, USA), followed by visualization on Bio Max MS film (Kodak, USA) at −80° C.

Example 3: Assessment of Invasion by ADCY3-Dependent Cell Migration and Control To overexpress ADCY3, HEK293 cells were transfected with pAcGFP1-ADCY3 vector, using Lipofectamine 2000 (Invitrogen), with the empty pAcGFP-C1 vector introduced as a negative control.

To silence the ADCY3 gene, $5 \times 10^4$ SNU-216 human gastric cancer cells were transfected with human ADCY3-specific siRNA (siADCY3: SI00058849 5'-ATGGAGCAC-CAGCTTCCTCAA-3' SEQ ID NO:1) or negative control (NC) siRNA (Cat. No. 1027280; Qiagen) in a 6-well culture plate by using HiPerfect (Qiagen).

To evaluate the protein expression of ADCY3, Western blotting was performed using anti-ADCY3 (ab14778; Abcam, Cambridge, UK), anti-GFP (sc-9996, Santa Cruz Biotechnology, USA), anti-CREB, anti-p-CREB Ser133 (#8212, Cell Signaling Technology, USA), anti-β-actin, and anti-α-tubulin (Sigma-Aldrich, St. Louis, Mo., USA).

Cell migration was assayed by staining cells that had migrated downward through an 8-μm pore filter insert (BD, USA) during an overnight incubation at 37° C. Crystal violet (1%) was used for cell staining, and $A_{564}$ measurements were made using a VERSAmax microplate reader (Molecular Devices, USA).

Invasion assays were performed by counting cells stained with Diff-Quick (Sysmex, Kobe, Japan) in Matrigel-coated inserts after 48 hr of incubation.

Clonogenicity was assayed by seeding $1 \times 10^3$ cells per well in 6-well plates and counting the viable colonies that were stained using Diff-Quick™, after a 7-day incubation.

Example 4: Quantification of cAMP

To confirm the function of expression of ADCY3 and its family members, examination was made of cAMP level increments depending on ADCY3 expression. HEK293 cells were transfected with 400 ng of pAcGFP or pAcGFP-ADCY3 by using Lipofectamine 2000, and seeded in 96-well plates at a density of $2 \times 10^4$ cells/well.

A cAMP level in 50 μL of cell lysate was measured using the CatchPoint cyclic-AMP Fluorescent Assay Kit (Cat# R8088, Molecular Devices) according to the manufacturer's protocol.

Example 5: Analysis of Promoter Methylation, and In Vitro Demethylation

To assay the methylation status of the ADCY3 promoter, genomic DNA was bisulfite-treated using the EZ DNA Methylation-Gold Kit (ZYMO Research, USA), and treated with methylation-specific PCR primers (Table 3) that were designed using EpiDesigner (Sequenom, USA).

A methylation-specific high-resolution melting assay (MS-HRM) was performed using 10 ng of bisulfite-treated genomic DNA and ResoLight dye in a LightCycler 480 (Roche Applied Science) according to the manufacturer's protocol. Results were analyzed using Gene Scanning software (Roche). For bisulfite sequencing, the promoter region containing 39 CpG sites was amplified from the genomic DNA of bisulfite-treated gastric cells, cloned into the TOPO-TA vector (Invitrogen), and sequenced using the 3730xl DNA analyzer (Applied Biosystems).

To investigate the effects of promoter demethylation on ADCY3 expression, KATO III cells were incubated for 96 hrs in a culture medium with or without 5-Aza-2'-deoxycytidine (5-Aza-dC; Sigma Aldrich, USA) at a final concentration of 10 μM, and the mRNA level of ADCY3 was measured using qRT-PCR.

TABLE 3

| Primer Name | Sequence (5'→3') | Sequence List |
|---|---|---|
| ADCY3-HRM1F | AAATAGAAGGAAGGTTTAGGAATTT | SEQ ID NO: 22 |
| ADCY3-HRM11R | TCCTATCCCTAACTTATAAAAAAC | SEQ ID NO: 23 |
| ADCY3-HRM2F | GGTTAGGTTTTTTTATAAGTTAGGGA | SEQ ID NO: 24 |
| ADCY3-HRM2R | CAAAACCTTCCCTACCACCC | SEQ ID NO: 25 |
| ADCY3-HRM2F | GTTGGGAGGTTTTTGTAGTAGAGAT | SEQ ID NO: 26 |
| ADCY3-HRM2R | AAAAAAAACCACCTCCAACAA | SEQ ID NO: 27 |
| ADCY3-BS-F | TTTTTAAGGGATAGTTTGTGAATTT | SEQ ID NO: 28 |
| ADCY3-BS-R | AACCCTATCCTACTCCCAAAAAAC | SEQ ID NO: 29 |

Example 6: Statistical Analysis

The statistical significance of data was determined using Student's t-test. P-values less than 0.05 were considered statistically significant. Differences between groups were calculated by Student's t-test.

Results

1. Elevated Expression of ADCY3 in Gastric Cancer

Comparison of gene expression profiles from microarray data between normal and tumor tissues of 27 gastric cancer patients revealed that ADCY3 was significantly upregulated in gastric cancer tissues, implying the applicability of ADCY3 as a diagnosis marker of gastric cancer. To validate this finding, examination was made of the relationship between the upregulation of ADCY3 and the development of human gastric cancer by measuring ADCY3 expression levels through qRT-PCR. ADCY3 mRNA levels in six human gastric cancer cell lines (SNU-216, SNU-638, SNU-719, AGS, KATO III, and MKN28) were significantly higher than those in normal cell lines (HDF, HMEC) (FIG. 1A). In addition, high mRNA levels of ADCY3 were confirmed in 19 of 21 Korean gastric cancer tissues (95%), and inter alia, 11 tissues (51.4%) exhibited significantly higher ADCY3 mRNA levels, compared to adjacent normal tissues (FIG. 1B).

Figure 1C:
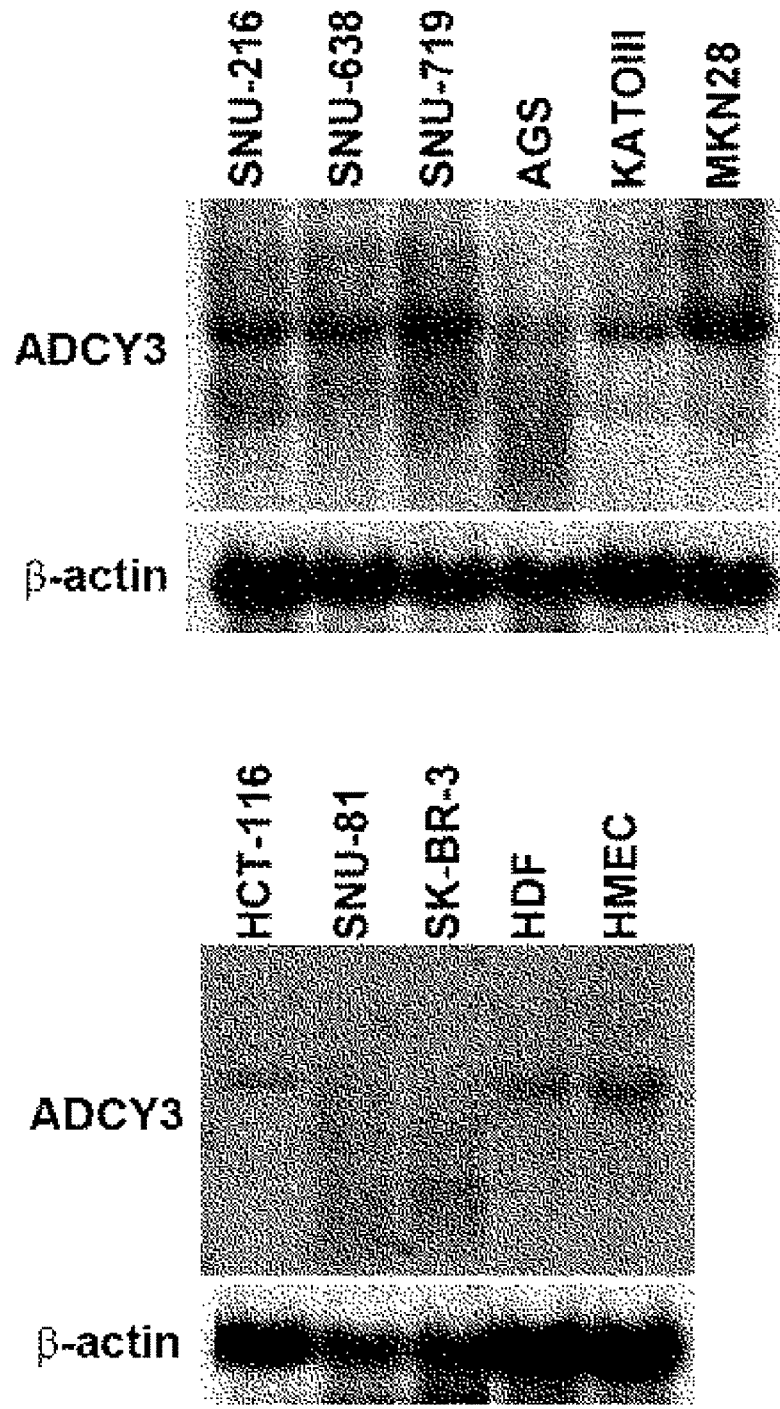
FIG. 1C shows the expression of ADCY3 mRNA in various human tissues.

Additionally, Northern blot analysis was performed to check for the presence of alternative spliced isoforms of ADCY3 in other cancer and normal cell lines. No splice variants were discovered. A single transcript of ADCY3 was detected at 4.4 kb, which is consistent with the mRNA size registered in the database (FIG. 1C).

2. Specificity of Upregulated ADCY3 Expression in Gastric Cancer

The ADCY family consists of 10 different members, which share high primary sequence homology at the catalytic site. Evolutionarily, ADCY3 is closer to ADCY2, ADCY4 and ADCY7, based on the analysis of sequences of their open reading frames by ClustralW. Prior to the analysis of ADCY3 expression in oncogenesis, expression data was examined to find out the correlation of primers among the ADCY family members. When the gastric cancer cell lines SNU-216, SNU-638, SNU-719, AGS, KATO III, and MKN28, and the normal cell lines HDF and HMEC were subjected to RT-PCR using primers specific for each family member, all the ADCY family members, but for ADCY3, showed no gastric cancer-specific expression patterns. Briefly, ADCY6 and ADCY7 were expressed in all the gastric cell lines as well as in both the normal cells while the other ADCY family members were not. Different combinations of the other ADCY family members were detected according to ADCY family members (FIG. 2). These findings suggest that all the ADCY family members are not expressed in gastric cell lines, with the sole gastric cancer-specific expression of ADCY3. Therefore, ADCY3 can be applicable as a gastric cancer-specific marker.

3. Role of ADCY3 in Gastric Cancer Tumorigenesis

To understand the function of the ADCY3 gene in gastric cancer development, ADCY3-overexpressing HEK293 cells were examined for cell migration and invasiveness. For HEK293 cells transfected with pAcGFP-ADCY3, the number of migrating cells significantly increased (P=0.01). Upon the overexpression of ADCY3, the migration increased by approximately 43%, as measured at $A_{564}$ (FIG. 3A). Consistent with the increase of cell migration, ADCY3-overexpressing cells showed a 4.95-fold increase in invasiveness (P=0.02) compared to cells transfected with the control vector (FIG. 3B). Collectively, these results demonstrate that the overexpression of ADCY3 incites cell migration and invasiveness. In addition, the effect of pAcGFP-ADC3 expression on anchorage-dependent cell growth was examined by a clonogenicity assay. Compared to the control transfected with an empty vector, pAcGFP-ADCY3-overexpressing cells exhibited a 1.5-fold reinforcement effect on anchorage-dependent cell growth (P<0.005) (FIG. 3C). These results suggest that ADCY3 confers a tumorigenic effect on gastric cells.

Figure 3F:
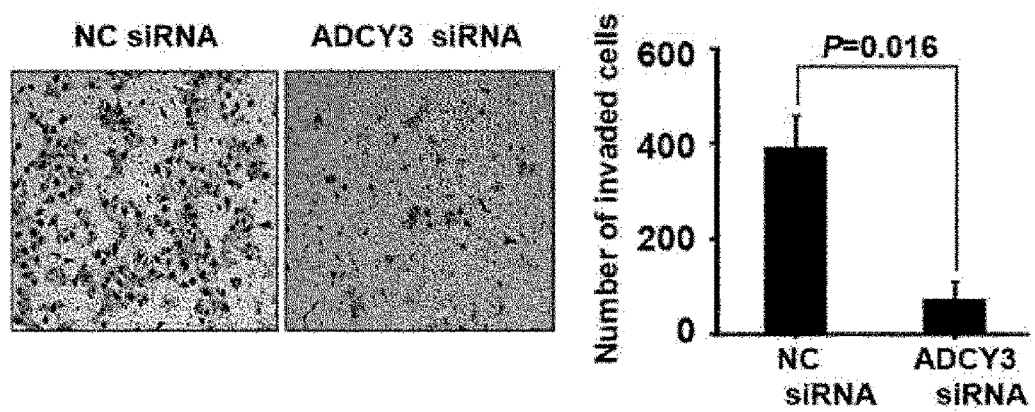
Figure 3G:
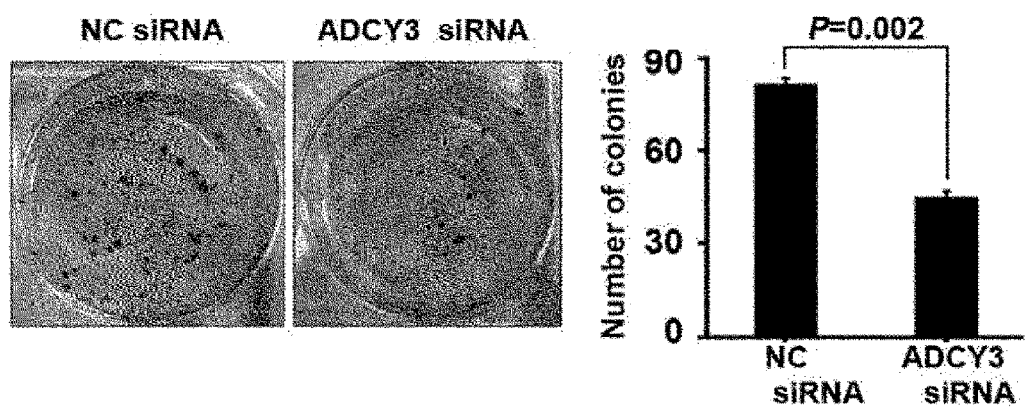

Examination was made to check whether the tumorigenesis-related effect of ADCY3 is inhibited by ADCY3-specific siRNA. For this, the SNU-216 gastric cancer cell line, found to overexpress ADCY3 in Examples 1 and 2, was treated with ADCY3-specific siRNA to examine whether the elevated tumorigenic potential of the cells is inhibited. Treatment with siRNA caused ADCY3 downregulation (FIG. 3D), and decreased cell migration by 21% (P=0.015) (FIG. 3E), and cell invasiveness by 5.29 fold (P=0.016) (FIG. 3F). In addition, clonogenicity was 1.8-fold decreased in the ADCY3 siRNA-treated cells, compared to negative control (NC) siRNA-treated cells (P=0.002) (FIG. 3G). This data accounts for the reduction of tumorigenesis-related effects by ADCY3 downregulation, demonstrating that ADCY3 accelerates the growth of tumor cells.

Figure 4:
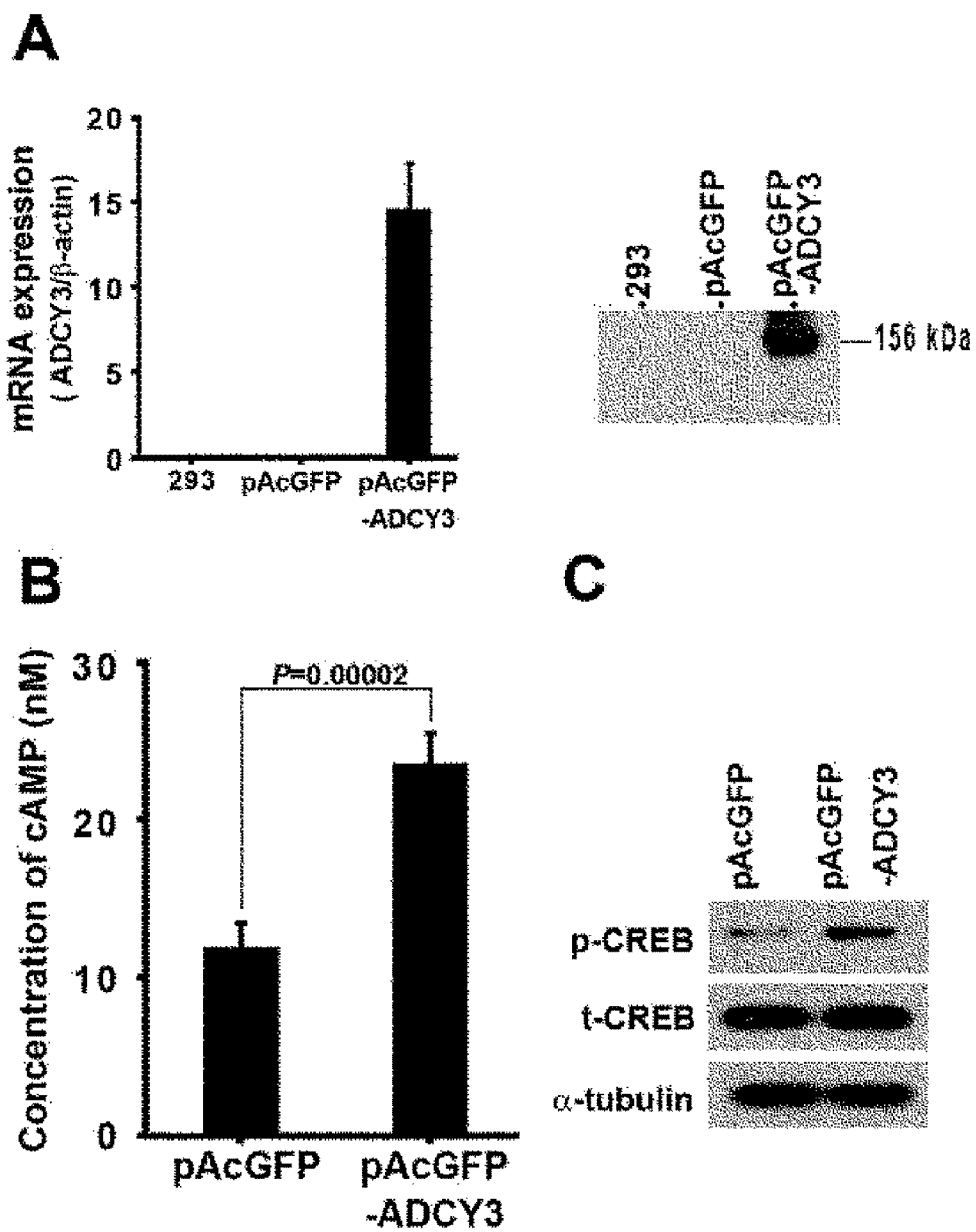
FIG. 4 shows an elevated level of mRNA and protein (A), cAMP (B), and p-CREB (C) in HEK293 cells transfected with an ADCY3 expression construct (pAc-GFP-ADCY3).

To understand the functional role of ADCY upregulation in gastric cancer tumorigenesis, cAMP levels in pAcGFP-ADCY3-transfected cells were measured. First, the overexpression of ADCY3 was confirmed by measuring an mRNA level using qRT-PCR, and a protein level using Western blotting (FIG. 4A). Then, HEK293 transfected with ADCY3 1.99-fold increased in cAMP concentration (P=0.00002) compared to a control transfected with an empty vector, indicating that ADCY3 overexpression affects cAMP formation (FIG. 4B). In this context, investigation was made of the effect of cAMP accumulation on the progression of gastric cancer by measuring CREB activity. To this end, the amounts of total CREB (t-CREB) and phosphorylated CREB (p-CREB) at the Ser133 residue were compared between cells transfected with an empty vector and a pAC-GFR-ADCY3 vector. Consistent with the observed changes in cAMP levels, the level of p-CREB was significantly higher in pAcGFP-ADCY3-transfected cells than that in control cells, whereas the level of t-CREB remained unchanged (FIG. 4C). These results suggest that ADCY3 promotes gastric cancer development via activation of cAMP-mediated CREB signaling.

4. Regulation of ADCY3 Expression by CpG Methylation in Promoter Region

Figure 5A:
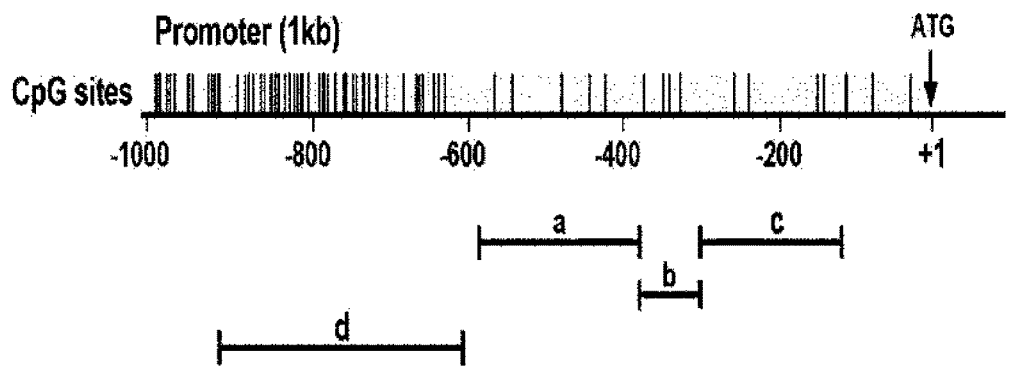
FIG. 5A shows a map of the CpG island in which DNA methylation status of ADCY3 in gastric cancer cell lines is analyzed (a, b, and c; region of MS-HRM screening, d; region of bisulfite sequencing).
Figure 5B:
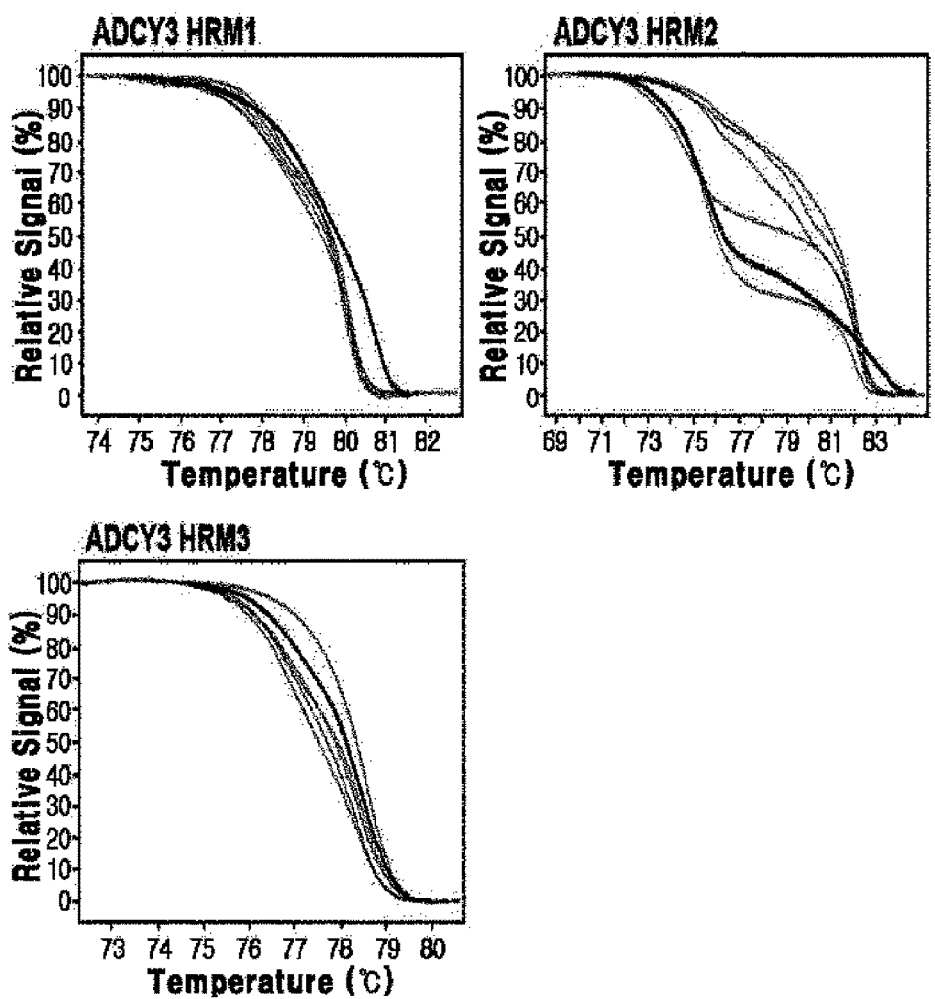
FIG. 5B shows results of HRM analysis in which HRM1, 2, and 3 are respectively consistent with a, b and c regions of FIG. 5A.
Figure 5C:
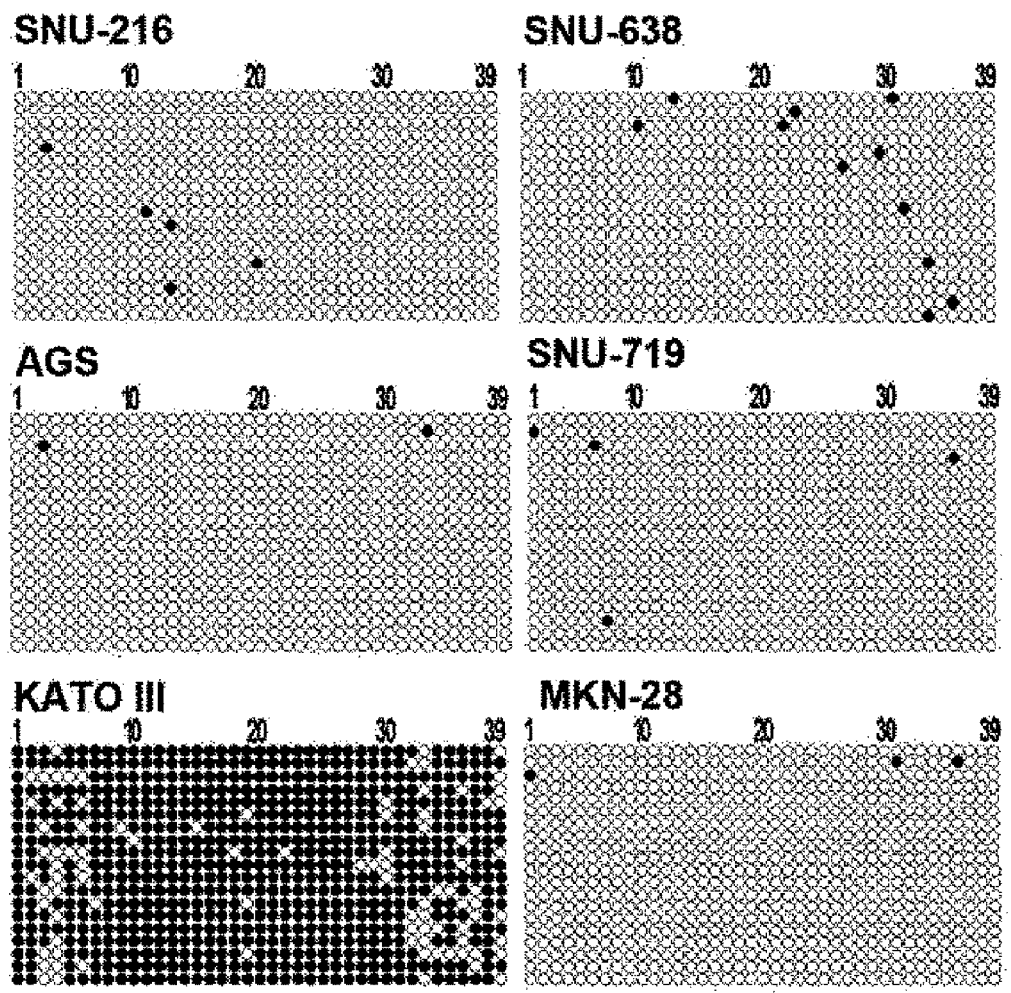
FIG. 5C shows results of bisulfite sequencing in which only the KATO-III cell line shows significant methylation on region d of panel A.
Figure 5D:
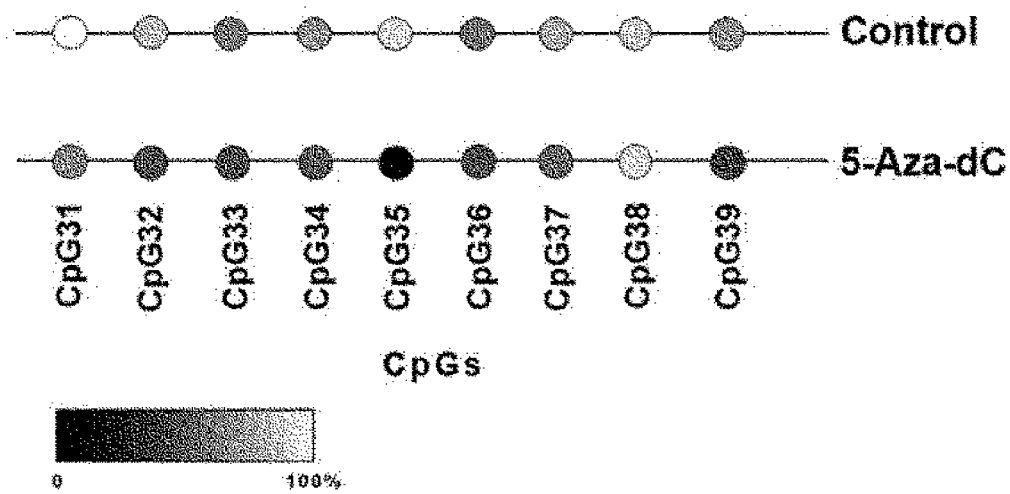
FIG. 5D shows the demethylation by 5-Aza-dC treatment reduced ADCY3 promoter methylation compared with negative control.
Figure 5E:
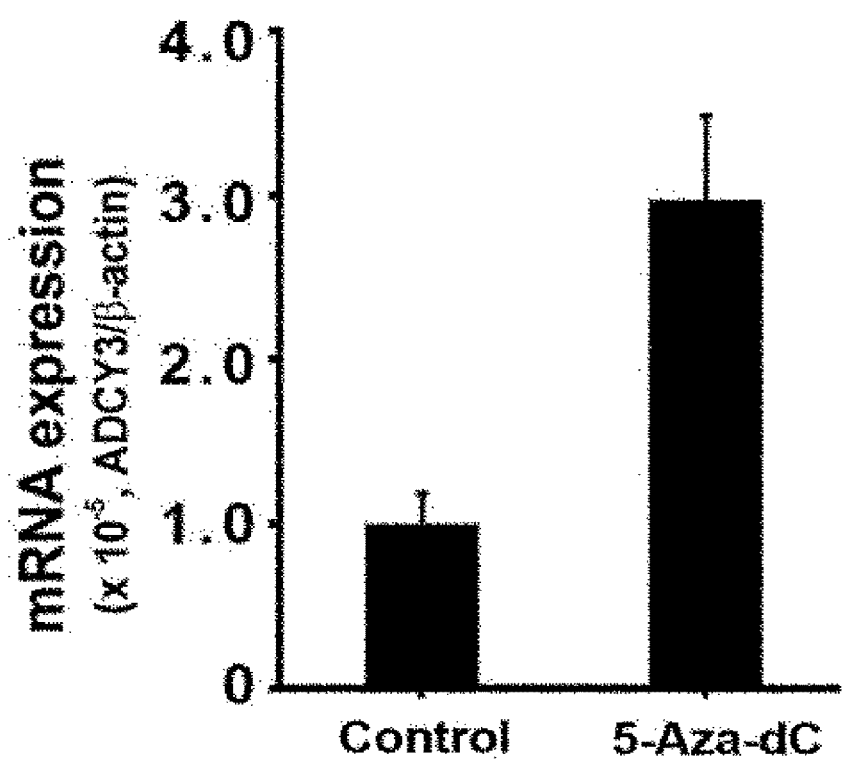
FIG. 5E shows restored ADCY3 expression in the KATOIII cell line according to qRT-PCR results.

The role of DNA methylation in the regulation of cancer-related gene expression has been well examined. In this experiment, investigation was therefore made to check whether ADCY3 expression is regulated by CpG methylation in the promoter region. First, methylation-sensitive high-resolution melting (MS-HRM) analysis was performed on a 1-kb ADCY3 promoter region immediately upstream of the translation start site. Because of the high density of CpG sites, however, three sets of primer pairs for amplifying PCR products spanning only the 457-bp region from 585 to 129 by upstream of the translational start site (ATG codon), and thus the region was analyzed by HRM (FIG. 5A). Clear differences in methylation level were not observed, which might be attributed to the fact that the region does not accurately contain the functional CpG islands (FIG. 5B). Hence, the region 694-387 by upstream of the translational start site, where a 308-bp CpG island was located, was analyzed by cloning and sequencing of bisulfite-treated DNA. Hypermethylation was observed in the ADCY3-non-expressing KATO III cell line whereas hypomethylation was observed in cell lines such as SNU-216, SNU-638, SNU-719, AGS, and MKN28, in which ADCY3 is highly expressed (FIG. 5C). The regulation of ADCY by CpG methylation in the promoter region was examined by treating the KATO III cell line with 5-Aza-2'-deoxycytidine (5-Aza-dC), a demethylating agent. This treatment resulted in demethylation of CpG sites, particularly, CpG sites 31-39, in the ADCY3 promoter (FIG. 5D), and the recovery of ADCY3 mRNA expression level, relative to the negative control, as analyzed by qRT-PCR (FIG. 5E). Taken together, these results suggest that DNA methylation of CpG islands in the promoter region regulates ADCY3 expression.

The invention claimed is:

1. A method for diagnosing gastric cancer, comprising:
   (a) providing a biological specimen obtained from a subject;
   (b) treating the biological specimen with an agent for assessing a methylation level of ADCY3 (Adenylate cyclase 3) gene, wherein the agent for assessing a methylation level of ADCY3 gene comprises:
      (i) bisulfite, and
      (ii) a primer pair specific for the ADCY3 gene sequence, wherein the primer pair specific for the ADCY3 gene sequence comprises SEQ ID NO: 28 and SEQ ID NO: 29;
   (c) amplifying a promoter region containing 39 CpG sites of the ADCY3 gene in the biological specimen treated with the agent;
   (d) assessing a methylation level of the promoter region of the ADCY3 gene in the biological specimen amplified according to (c);
   (e) comparing the assessed methylation level of the promoter region of the ADCY3 gene in (d) with a normal control; and
   (f) diagnosing gastric cancer if the assessed methylation level is lower than that of the normal control.

* * * * *